United States Patent
Kwirandt

(10) Patent No.: US 8,004,667 B2
(45) Date of Patent: Aug. 23, 2011

(54) INSPECTION APPARATUS FOR CONTAINERS

(75) Inventor: Rainer Kwirandt, Barbing (DE)

(73) Assignee: Krones AG (DE)

( * ) Notice: Subject to any disclaimer, the term of this patent is extended or adjusted under 35 U.S.C. 154(b) by 101 days.

(21) Appl. No.: 12/303,583

(22) PCT Filed: Sep. 27, 2007

(86) PCT No.: PCT/EP2007/008408
§ 371 (c)(1),
(2), (4) Date: Dec. 5, 2008

(87) PCT Pub. No.: WO2008/040487
PCT Pub. Date: Apr. 10, 2008

(65) Prior Publication Data
US 2010/0225908 A1    Sep. 9, 2010

(30) Foreign Application Priority Data
Oct. 5, 2006    (DE) .......................... 10 2006 047 150

(51) Int. Cl.
*G01N 21/00* (2006.01)
(52) U.S. Cl. .................. 356/239.4; 250/576; 250/222.2; 250/223 B; 356/237.2; 356/239.1; 356/239.7
(58) Field of Classification Search .............. 356/237.1, 356/237.2, 237.3, 239.4, 239.1, 239.8, 240.1, 356/239.5, 239.7; 250/576, 222.2, 223 R, 250/223 B
See application file for complete search history.

(56) References Cited

U.S. PATENT DOCUMENTS

| | | | | |
|---|---|---|---|---|
| 4,943,713 A | * | 7/1990 | Yoshida | ..................... 250/223 B |
| 6,061,125 A | * | 5/2000 | Thomas et al. | ............. 356/239.4 |

FOREIGN PATENT DOCUMENTS

| | | |
|---|---|---|
| DE | 2848219 A1 | 5/1980 |
| DE | 3233919 A1 | 9/1982 |
| DE | 3611536.3 A1 | 10/1987 |
| DE | 3839682 A1 | 6/1989 |
| DE | 19914028 C1 | 9/2000 |
| DE | 10065290 C2 | 7/2002 |
| DE | 102005044206.4 A1 | 3/2007 |
| EP | 0387930 A1 | 9/1990 |
| EP | 0628807 A1 | 12/1994 |
| JP | 5764153 A | 4/1982 |
| WO | 02054051 A2 | 7/2002 |

OTHER PUBLICATIONS

International Search Report issued in corresponding PCT Application, Serial No. PCT/EP2007/008408.

* cited by examiner

*Primary Examiner* — Gregory J Toatley
*Assistant Examiner* — Iyabo S Alli
(74) *Attorney, Agent, or Firm* — Mills & Onello, LLP

(57) ABSTRACT

An inspection apparatus for containers, comprising a first illumination device which directs light having first characteristic properties onto the base of the container, a second illumination device which directs light having second characteristic properties, which differ at least partially from the first characteristic properties, onto the base of the container, and at least one image recording device which receives at least a portion of the light directed onto the base of the container and transmitted by the latter. At least the second illumination device illuminates the base of the container in an indirect manner.

18 Claims, 1 Drawing Sheet

INSPECTION APPARATUS FOR CONTAINERS

Figure 1:
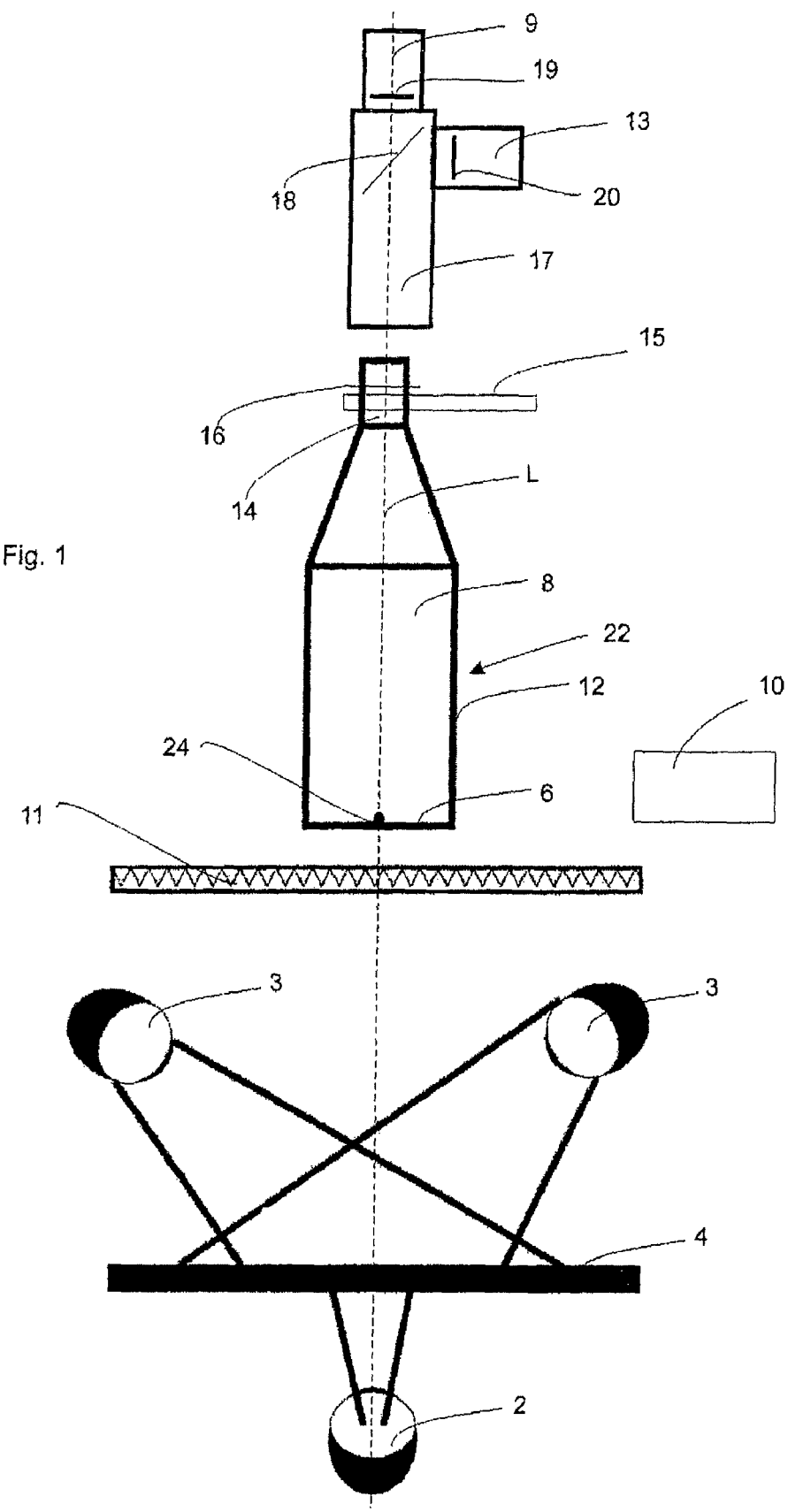

The present invention relates to an inspection apparatus for containers. The invention will be described with reference to plastic bottles or preforms; however, it is pointed out that the invention can also be used for other transparent or semi-transparent containers or hollow bodies. Such inspection apparatuses are known from the prior art. In so-called stretch blow-moulding machines, it is necessary to check the respectively produced containers. Such an apparatus for the optical inspection of bottles is known for example from DE 100 652 90 A1. In said document, in particular the bases of the containers are very relevant for an inspection, since here for example a centering check of the injection point of the hollow bodies can be carried out. For example, DE 199 140 28 C1 describes an apparatus for checking the precise position of the injection point in relation to a container. The document DE 10 2005 044 206.4, which has not yet been published, describes a method for checking the quality of a stretch blow-moulded plastic container. Here, the density of the light is used to examine the container base. The subject matter of DE 10 2005 044 206.4 is hereby fully incorporated by way of reference into the subject matter of the present application.

As is known, a check of the containers and in particular of the bases thereof with regard to different criteria is possible using different examination methods and radiation sources. However, the problem arises that, in stretch blow-moulding machines, the distance or time within which an inspection is possible is very short, since further units such as a sterilisation and/or filling station adjoin the stretch blow-moulding machine at a very short physical and/or temporal distance therefrom. In this case, transfer members in the form of star wheels and/or chains with suitable holding devices are arranged between the individual workstations, and a check of the containers or of the bases thereof has to take place in the short section between the stretch blow-moulding machine and for example the machine located immediately downstream. In the time available, therefore, a check of the containers has to be carried out both with regard to the freedom from defects (cracks, bubbles, foreign bodies) and with regard to the manufacturing quality (material distribution, wall thickness, etc.), and a decision has to be made as to whether a certain container passes to the next workstation of the production process or is rejected. At the required machine capacities of up to 60,000 containers/hour, it is often not possible to arrange two different inspection apparatuses within the short distance in such a way as to have sufficient time for the analysis and for any discarding of containers before entering the next treatment device.

The object of the present invention is therefore to provide an inspection apparatus which allows a more varied check of the containers within approximately the same time or less.

This is achieved according to the invention by an apparatus according to claim 1 and by a method according to claim 18. Advantageous embodiments and further developments form the subject matter of the dependent claims.

The inspection apparatus for containers according to the invention comprises a first illumination device which directs light having first characteristic properties onto the base of the container. Provided in addition to this is a second illumination device which directs light having second characteristic properties, which differ at least partially from the first characteristic properties, onto the base of the container. Also provided is at least one image recording device which receives at least a portion of the light directed onto the base of the container and transmitted by the latter.

According to the invention, the second illumination device illuminates the base of the container in an indirect manner. Indirect illumination is understood here to mean that the light coming from the second illumination device does not impinge on the base of the container via a direct route and in particular with a rectilinear beam path, but rather firstly impinges on a further medium and only the light scattered by this medium impinges on the base of the container. Removing this intermediate medium would therefore mean that the second illumination device no longer illuminates the base of the container.

By virtue of this indirect illumination, diffuse light can be produced in a particularly advantageous manner, which then impinges on the base of the container. The first illumination device illuminates the base of the container with at least partially directional radiation and therefore not with completely diffuse light.

Preferably, the inspection apparatus comprises a scattering device which is illuminated by the second illumination device, wherein the light scattered by this scattering device impinges at least partially on the base of the container.

Advantageously, the second illumination device, i.e. the illumination device which illuminates the base of the container in an indirect manner, is arranged between the scattering device and the base of the container. In this way, it can be achieved in a particularly advantageous manner that only scattered light from the scattering device impinges on the base of the container, but not direct illumination from the second illumination device. In this case, the emission direction of the second illumination device may face away from the base of the container. In a further preferred embodiment, the second illumination device emits white light. To this end, it is possible on the one hand to use a plurality of white light-emitting diodes; with particular preference, however, use is made of a plurality of red, blue and green light-emitting diodes which as a whole emit light which approximates white light.

In a further preferred embodiment, the second illumination device illuminates the scattering device in a divergent or widened manner. In other words, the light of the second illumination device is widened and thus illuminates the scattering device over a large surface area. In a further preferred embodiment, the scattering device is arranged between the first illumination device and the base of the container. This means that the first illumination device illuminates the base of the container through the scattering device and thus illuminates said base in a direct manner. Preferably, the first illumination device produces a light spot on the scattering device, in order in this way to ensure that directional radiation or only weakly diffuse light impinges on the base of the container. A small opening in the scattering device for a free, non-scattered passage of the directional light of the first illumination device would also be conceivable.

Preferably, a lens device is arranged between the illumination devices and the base of the container in order to project an image onto the observation device. Said lens device may in particular be a Fresnel lens.

Preferably, a separating device is provided, by means of which the light of the first illumination device which has been received by the image recording device and the light of the second illumination device which has been received by the image recording device are or can be substantially completely separated from one another. Besides the term "image recording device", the term "camera" will also be used below.

By virtue of this embodiment, two different optical measurement methods are carried out by one inspection apparatus, and thus it is possible to save space and time or to carry out a more extensive inspection within the same amount of space and time. The ability for complete separation of the types of light is understood to mean that the image recording device can output signals which are influenced only by the light from the first illumination device, and also signals which are influenced only by the light from the second illumination device. The separation of the two types of light may take place in various ways, as will be explained in more detail below.

Preferably, the separating device comprises a control device which causes the light of the first illumination device and the light of the second illumination device to impinge on the base of the container in an at least partially temporally offset manner. In this embodiment, a separation of the two types of light or illumination is achieved via the temporal offset thereof, i.e. the at least one camera records the two types of illumination in a temporally offset manner. Preferably, the two types of light are directed onto the base of the container and thus onto the image recording device in a temporally offset manner, i.e. without temporal overlaps.

In a further embodiment, the two illumination devices direct light of different wavelengths onto the base of the container and, by means of the separating device, the light of the first wavelength which has been received by the image recording device and the light of the second wavelength which has been received by the image recording device can be substantially completely separated from one another. The same is conceivable for differently polarised light (e.g. polarised in a linear or circular manner).

Here, too, different embodiments of separating devices are conceivable. For instance, it would be conceivable that filters or mirrors are provided which allow the light of one wavelength to pass through and which reflect the light of the other wavelength and direct it for example onto a second camera. For this, mirror systems are known which allow a substantially complete separation of light of different wavelengths. Besides this, a separation may also be carried out by the camera itself, for example by providing a colour camera which splits the recorded image into two images with different colour components. In this case, therefore, no temporal offset between the two light pulses is necessary; however, this can additionally be used to improve the separation.

In addition, a separation of the light sources may also take place via other measures, such as a separation of different polarisation directions for example. Preferably, however, this separation takes place once the light has already passed through the container base.

The two types of light emitted by the two illumination devices therefore differ at least in one property apart from any different wavelengths. By way of example, one type of light is diffuse light and the other type of light is more directional or less diffuse radiation. As mentioned above, different characteristics of the container can be examined by means of these different types of illumination. Specifically, it is possible to examine the base quality of the container by means of directional radiation. For example, it is possible to measure the characteristic material distributions in the base of the container and to determine characteristic parameters from this, such as for example the surface areas of a non-stretched or only slightly stretched region on the base of the container and/or the size and position of a transition region between a non-stretched and a stretched region. By using the directional light, it is thus possible in a simple manner to provide a parameter which is highly indicative of the quality of the stretch blow-moulding process and/or the quality of the stretch blow-moulded plastic container.

When stretching the base of a plastic container, different characteristic material distributions occur in the base depending on the process control. These inhomogeneities can be accentuated by the directional illumination according to the invention and can be recorded using electronic camera technology. If, for example, the inner wall and the outer wall in the container base are not parallel to one another, for example since material curvatures or inhomogeneities occur, a wedge angle occurs between the inner wall and the outer wall. As a result, the directional light is deflected by refraction and does not reach the camera, as a result of which such regions appear darker on the camera image.

In a further embodiment, instead of or in addition to directional light, it is possible to use polarised light in order for example to carry out a detection of material stresses. In addition, in the case of coloured container materials, inhomogeneities can be made obvious through the absorption of light in the visible wavelength range. A detection of the absorption of visible light through coloured plastic material therefore takes place.

The second illumination device emits, preferably via the scattering device, preferably diffuse or non-directional light. With this type of light, it is possible to examine for example the base in order to measure for example the geometric location of an injection point. In a further preferred embodiment, at least one illumination device is arranged below the container in the longitudinal direction of the container. The image recording device is advantageously a camera with a lens and is particularly preferably arranged above the bottle. That is to say that, in this embodiment, the base of the container is inspected using the transmitted light method. By arranging an illumination device and particularly preferably the first illumination device in the longitudinal direction of the container below the latter, a direct illumination of the base is possible by the first illumination device without using further elements such as mirrors.

Preferably, both illumination devices are arranged in such a way that the light emitted by them impinges substantially in the longitudinal direction on the base of the container. The types of light coming from the two illumination devices or the beam paths impinging on the base of the container are thus preferably coaxial to one another. Specifically, the light of the second illumination device, which is scattered by the scattering device, does not impinge with a unitary emission direction on the base of the container. Instead, the individual directions are randomly distributed. On average, however, an emission direction is once again obtained which runs approximately in the longitudinal direction of the container. To this end, the surface area of the scattering device which is illuminated by the second illumination device is preferably selected to be concentric with respect to the surface of the base of the container. It is possible in this case to deflect the light of the second illumination source for example by means of a deflection mirror in such a way that it impinges on the base of the container substantially in the longitudinal direction. By virtue of the apparatus according to the invention, a checking of containers, in particular of the PET base quality and the conventional PET base inspection by means of diffuse light can take place in combination in one station. A more compact construction is thus possible, without restricting the inspection possibilities.

For said base inspection, as already mentioned, a diffuse or soft illumination of the container base from below is used so that on the one hand the injection point can be measured precisely and on the other hand small opaque inclusions and white crystalline regions can be made visible. As mentioned above, on the other hand relatively small unevennesses and wall thickness fluctuations can be suppressed when using the second illumination device. By contrast, the measurement of the PET base quality is based on a more directional or hard illumination of the base from below.

Preferably, the inspection apparatus comprises at least one evaluation device which determines a relative position of at least one region of a wall of the container with respect to an injection point of the container. This evaluation device therefore uses data which are obtained from the illumination with diffuse light.

Preferably, the control device causes the light of the first illumination device and the light of the second illumination device to be offset with respect to one another by between 200 µs and 1500 µs, preferably by between 200 µs and 1000 µs and particularly preferably by between 300 µs and 600 µs. A typical value for this temporal offset is up to 500 µs. By virtue of this slightly temporally offset actuation of the illumination devices, the container base can be illuminated within a relatively short time window of approximately 1 ms. In any case, the temporal offset of the types of illumination means that the recordings of the two light sources do not influence one another or influence one another only slightly. The two illumination devices are thus preferably pulsed light sources, for example light-emitting diodes which emit pulses.

The image recording device is advantageously a double-exposure camera, i.e. a camera which can output two images within very short time intervals.

In a further particularly preferred embodiment, the inspection apparatus comprises a second image recording device. Preferably two separate cameras are thus provided. In this case, it is once again possible to provide a beam splitter, such as a partially transparent mirror for example, in a beam path between the container and the cameras. A beam-splitting double lens could also be provided. The guidance of the containers and the individual recording operations otherwise take place in the same way as in the case of inspection devices known from the prior art. Preferably, the illumination devices emit visible light and in particular visible light of different wavelengths. A separation of the two types of illumination can thus also be carried out via additional filters, such as RG filters or the like. However, it is also possible that one illumination device or even both illumination devices emit white light. With particular preference, the illumination devices comprise white LEDs as light sources, or LEDs of different colour so as thus to produce white light.

In a further preferred embodiment, the first illumination device comprises a point light source. This may for example emit light which is directed by means of a reflector, that is to say light comprising substantially parallel light beams. In addition, however, it is also possible to use optical elements such as lenses or the like in order to direct the light. Preferably, the second illumination device comprises a plurality of light sources. In this case, with particular preference an illumination is used which covers a large surface area, for example in the form of a plurality of light-emitting diodes which are arranged in an array.

The present invention also relates to a stretch blow-moulding machine comprising an inspection apparatus of the type described above, wherein the inspection apparatus is preferably integrated in the discharge region of the machine, for example at the periphery of a discharge star wheel.

The invention also relates to a method for inspecting containers and in particular stretch blow-moulded plastic containers by optical inspection of the base of the containers. Here, in a first method step, the base of the container is illuminated by a first illumination device by means of light having first characteristic properties. The base of the container is also illuminated by a second illumination device by means of light having second characteristic properties which differ from the first characteristic properties. Furthermore, at least a portion of the light directed onto the base of the container from the two illumination devices is received by at least one image recording device. According to the invention, the base of the container is illuminated by the second illumination device in an indirect manner.

Preferably, a scattering device is provided which is illuminated by the second illumination device and which in turn throws scattered light onto the base of the container. Preferably here too, the second illumination device is arranged between the scattering device and the base of the container.

Preferably, the light of the first illumination device which has been received by the image recording device and the light of the second illumination device which has been received by the image recording device can be substantially separated from one another or are substantially completely separated from one another.

Advantageously, the light of the first illumination device and the light of the second illumination device are directed onto the base of the container in a manner temporally offset with respect to one another. By virtue of this temporal offset, it is also possible to carry out two different measurement methods within a relatively short period of time and thus within the relatively short period of time available for the inspection method.

In a further preferred embodiment, the illumination devices direct light of different wavelengths onto the base of the container, and the light of a first wavelength which has been received by the image recording device and the light which has been received by the second image recording device are substantially completely separated from one another.

Preferably, quality features of the container are derived from the recorded images by means of image processing algorithms, wherein in particular electronic CCD cameras with spatial resolution are used for image recording. Preferably, the illumination illuminates the base of the container and the image recording device looks through the mouth opening of the container towards the base thereof, so that a transmitted light method is carried out.

With particular advantage, the surface area of a non-stretched or only slightly stretched overall region or of a selected non-stretched or only slightly stretched sub-region on the base of the container is determined by using the light having the first characteristic properties. Through the recording process, quality features of the container are derived and with particular preference are compared with predefined limit values and, in the event of exceeding the limit values, trigger rejection of the container in question. Preferably, the light used is visible light. However, it is also possible to use other types of light, such as infrared or ultraviolet light or combinations thereof.

Preferably, after passing through the base, the light runs through a beam-splitting device. The light having the first characteristic properties and the light having the second characteristic properties can thus be separated from one another. In addition, the light can in this way also be split into two parts (each having the same characteristic properties) and passed to two cameras.

Further advantages and embodiments will emerge from the appended FIGURE, in which:

FIG. 1 shows a schematic view of the inspection apparatus according to the invention.

FIG. 1 shows an inspection apparatus according to the invention for inspecting a container 8. This container (for example a transparent plastic bottle made from PET) is guided here by a so-called neck handling clamp 15. The container 8 is designed with substantial rotation symmetry relative to a longitudinal axis L. The wall 12 of the container 8 has a mouth region 14 which is provided with an external thread and which has a laterally protruding support ring 16 (not shown in greater detail). Provided below the support ring 16 is a laterally protruding, substantially cylindrical body region 22 which forms the largest outer diameter of the container 8. This body region opens into a base 6 which is designed as a standing face. Located on the outside of the base is an injection point 24, which is normally central.

Two illumination devices 2 and 3 are provided below the base or the container 8. Here, the second illumination device 3 comprises an illumination which covers a large surface area, which may comprise for example a plurality of light-emitting diodes across an ample surface. Furthermore, a preferably conical ring of illumination devices could also be provided. The light of the illumination device 3 is emitted onto a scattering device 4, which may be for example a sheet of matte or frosted glass. Here, the light of the illumination device 3 is widened in order to achieve an illumination of the scattering device 4 over a large surface area. The light scattered by the scattering device passes via a lens device 11 onto the base of the container. However, no light thus passes from the illumination device 3 to the base of the container in a direct manner, i.e. without passing through the scattering device 4.

Reference 2 denotes the first illumination device, which may be for example an LED spotlight (for examining the PET base quality). This illumination device 2 illuminates the scattering device in a point or spot fashion and thus produces more directional light which reaches the base 6 of the container 8. The illumination device 2 thus produces from below a small spot in the centre of the scattering device. As a result, a very hard light is produced. By virtue of a variable distance of the illumination device 2 from the scattering device 4, the spot size and thus the hardness of the light can be changed. The optimal image contrast for the base quality can thus be set.

By illuminating the scattering device 4 from above by means of the illumination device 3, a much softer light is produced for the normal base check. This light is also variable. Preferably, a large diaphragm can be placed over the scattering device, which thus reduces the size of the light area and thus allows somewhat harder light. However, since soft light is required in this case, preferably the hole in this diaphragm is always selected to be large enough that it does not influence the first illumination from below.

A combination of two types of illumination of different hardness can thus be obtained at the same location on the base, which types of illumination can moreover still be finely tuned independently of one another.

In a further advantageous variant, the illumination of the scattering device 4 may be structured. For example, an illuminating ring produces quasi a negative image, or an asymmetric light distribution produces images with a 3D effect.

The lens device 11, e.g. Fresnel lens, images the centre of the scattering device 4 onto the camera lens. This scattering device is then illuminated by the two above-described illumination devices in quick succession.

A control device 10 causes the two illumination devices 2 and 3 to emit their light in a manner temporally offset with respect to one another. Provided above the container 8 are two image recording devices 9 and 13 in the form of two cameras, which preferably comprise CCD chips. The cameras are preferably designed to output colour images. In this case, a beam splitter 18 is provided which causes both cameras 9, 13 to be illuminated. Preferably, the beam splitter is designed in such a way that the light of one illumination device 2, 3 reaches one camera 9, 13 and the light of the other illumination device 3, 2 reaches the other camera 13, 9. In this embodiment, the illumination devices 2, 3 and the associated cameras 9, 13 are advantageously synchronised with one another in each case.

Reference 17 denotes a combined lens or double lens with the beam splitter 18 arranged therein. The scattering device may also cause the types of illumination and the cameras to be actuated in a slightly temporally offset manner, and thus two different recordings can take place at almost the same container position without influencing one another. Overall, therefore, two recordings using different types of light can be carried out within a relatively short time window, and the container can thus be examined with regard to at least two different criteria.

For the inspection apparatus according to the invention, essentially no more room or space is necessary than for corresponding inspection apparatuses from the prior art. A plurality of inspection tasks can thus be carried out by the inspection apparatus according to the invention without losing any time or requiring further space.

References 19 and 20 denote filters which may be arranged in each case in the beam paths between the beam splitter 18 and the cameras 9, 13 in order to separate light of different wavelengths.

All of the features disclosed in the application documents are claimed as essential to the invention in so far as they are novel individually or in combination with respect to the prior art.

The invention claimed is:

1. Inspection apparatus for containers, comprising:
a first illumination device which directs light having first characteristic properties onto a base of the container;
a second illumination device which directs light having second characteristic properties, which differ at least partially from the first characteristic properties, onto the base of the container;
at least one image recording device which receives at least a portion of the light directed onto the base of the container and transmitted by at least one of the first and second illumination devices, wherein at least one of the first and second illumination devices illuminates the base of the container in an indirect manner; and
a scattering device that is illuminated by at least one of the first and second illumination devices, wherein the at least one of the first and second illumination devices that illuminates the base of the container in an indirect manner is arranged between the scattering device and the base of the container.

2. Inspection apparatus according to claim 1, wherein the light emitted by the at least one of the first and second illumination devices that illuminates the base of the container in an indirect manner is scattered by the scattering device and impinges at least partially on the base of the container.

3. Inspection apparatus according to claim 2, wherein the at least one of the first and second illumination devices that illuminates the base of the container in an indirect manner illuminates the scattering device in a divergent manner.

4. Inspection apparatus according to claim 2, wherein the scattering device is arranged between the first illumination device and the base of the container.

5. Inspection apparatus according to claim 1, wherein the second illumination device emits white light.

6. Inspection apparatus according to claim 1, further comprising a separating device that operates to substantially separate from one another the light of the first illumination device which has been received by the at least one image recording device and the light of the second illumination device which has been received by the at least one image recording device.

7. Inspection apparatus according to claim 6, wherein the separating device comprises a control device which causes the light of the first illumination device and the light of the second illumination device to impinge on the base of the container in an at least a partially temporally offset manner.

8. Inspection apparatus according to claim 7, wherein the control device causes the light of the first illumination device and the light of the second illumination device to be temporally offset with respect to one another by at least one of between about 200 μs and about 1500 μs, between about 200 μs and about 1000 μs and between about 300 μs and about 600 μs.

9. Inspection apparatus according to claim 6, wherein the light having the first characteristic properties and the light having the second characteristic properties have different wavelengths in addition to the different properties, wherein, the separating device operates to substantially separate from one another the light of a first wavelength which has been received by the at least one image recording device and the light of a second wavelength which has been received by the at least one image recording device.

10. Inspection apparatus according to claim 1, wherein the first illumination device emits substantially directional radiation and the second illumination device emits diffuse light.

11. Inspection apparatus according to claim 1, wherein at least one of the first and second illumination devices is arranged below the container in a longitudinal direction of the container.

12. Inspection apparatus according to claim 11, wherein both the first and second illumination devices are arranged so that their respective emitted light impinges in each case substantially in the longitudinal direction on the base of the container.

13. Inspection apparatus according to claim 1, further comprising at least one evaluation device which determines a relative position of at least one region of a wall of the container with respect to an injection point of the container.

14. Inspection apparatus according to claim 1, further comprising a second image recording device.

15. Inspection apparatus according to claim 1, wherein the first illumination device comprises a point light source.

16. A stretch blow-moulding machine comprising an inspection apparatus according to claim 1.

17. A method for inspecting containers by optical inspection of the base of the container, comprising:
    illuminating a base of the container by a first illumination device emitting light having first characteristic properties;
    illuminating the base of the container by a second illumination device emitting light having second characteristic properties which differ from the first characteristic properties;
    receiving, at at least one image recording device, at least a portion of the light directed onto the base of the container from at least one of the first and second illumination devices, wherein the base of the container is illuminated by the second illumination device in an indirect manner; and
    illuminating a scattering device by at least one of the first and second illumination devices, wherein the second illumination device that illuminates the base of the container in an indirect manner is arranged between the scattering device and the base of the container.

18. The method according to claim 17, wherein the light of the first illumination device which has been received by the at least one image recording device and the light of the second illumination device which has been received by the at least one image recording device are substantially separated from one another.

* * * * *